(12) United States Patent
Yanagisawa

(10) Patent No.: US 10,317,378 B2
(45) Date of Patent: Jun. 11, 2019

(54) DATA PROCESSING SYSTEM AND DATA PROCESSING METHOD FOR CHROMATOGRAPH

(71) Applicant: SHIMADZU CORPORATION, Kyoto-shi, Kyoto (JP)

(72) Inventor: Toshinobu Yanagisawa, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 809 days.

(21) Appl. No.: 14/649,580

(22) PCT Filed: Oct. 31, 2013

(86) PCT No.: PCT/JP2013/079533
§ 371 (c)(1),
(2) Date: Jun. 4, 2015

(87) PCT Pub. No.: WO2014/087770
PCT Pub. Date: Jun. 12, 2014

(65) Prior Publication Data
US 2015/0308992 A1    Oct. 29, 2015

Related U.S. Application Data

(63) Continuation of application No. PCT/JP2013/079533, filed on Oct. 31, 2013.

(30) Foreign Application Priority Data

Dec. 7, 2012 (JP) .................... 2012-267981

(51) Int. Cl.
*G01N 30/72* (2006.01)
*G01N 30/74* (2006.01)
*G01N 30/86* (2006.01)

(52) U.S. Cl.
CPC ..... *G01N 30/7233* (2013.01); *G01N 30/8675* (2013.01); *G01N 30/8689* (2013.01); *G01N 30/74* (2013.01)

(58) Field of Classification Search
USPC .......................................... 702/25
See application file for complete search history.

(56) References Cited

U.S. PATENT DOCUMENTS 5,596,135 A * 1/1997 Mito .................. G01N 30/8624
                                                                702/179
6,393,368 B1 * 5/2002 Ito ..................... G01N 30/8624
                                                                 702/22

(Continued)

FOREIGN PATENT DOCUMENTS

JP    10132799 A  *  5/1998
JP    11295289 A  * 10/1999

OTHER PUBLICATIONS

Machine Tranlsation of JP 11295289 from JPO site.*

(Continued)

*Primary Examiner* — Mohamed Charioui
*Assistant Examiner* — Terence E Stifter, Jr.
(74) *Attorney, Agent, or Firm* — Sughrue Mion, PLLC

(57) ABSTRACT

A data processing system including a sensitivity coefficient holder for holding a value R of a sensitivity coefficient for a wavelength $\lambda 1$ belonging to one peak in a spectrum of a first component and a second wavelength $\lambda 2$ belonging to the same peak and having a lower intensity than $\lambda 1$, the value R defined using the ratio of the peak areas or similar information of two chromatograms respectively obtained at the two wavelengths; a chromatographic detector for spectroscopically analyzing sample components exiting from a component-separating column and for measuring an intensity at the second wavelength $\lambda 2$ of the spectrum of the first component and an intensity at a wavelength $\lambda 3$ of a spec- (Continued)

trum of a second component at each point in time; and a concentration ratio calculator for calculating the ratio of concentration between the first component and the second component.

10 Claims, 6 Drawing Sheets

(56) References Cited

U.S. PATENT DOCUMENTS

| | | | |
|---|---|---|---|
| 6,629,039 B1* | 9/2003 | Wang | G01N 30/8689 |
| | | | 702/22 |
| 2010/0050737 A1* | 3/2010 | Wolters | G01N 30/8665 |
| | | | 73/23.22 |
| 2014/0156201 A1* | 6/2014 | Mori | G01N 30/8675 |
| | | | 702/23 |
| 2014/0190243 A1* | 7/2014 | Gunji | G01N 30/74 |
| | | | 73/61.55 |
| 2014/0257712 A1* | 9/2014 | Mito | G01N 30/74 |
| | | | 702/25 |

OTHER PUBLICATIONS

Machine Tranlsation of JP 10132799 from JPO site.*
Ritsuo Hosokawa, "The Ministry of Health, Labour and Welfare Ministerial Notification No. 65", The Japanese Pharmacopoeia, Sixth Edition, Mar. 24, 2011, pp. 1-2319 (accessed on Sep. 25, 2012 from Internet).
International Search Report for PCT/JP2013/079533 dated Jan. 21, 2014 [PCT/ISA/210].

* cited by examiner

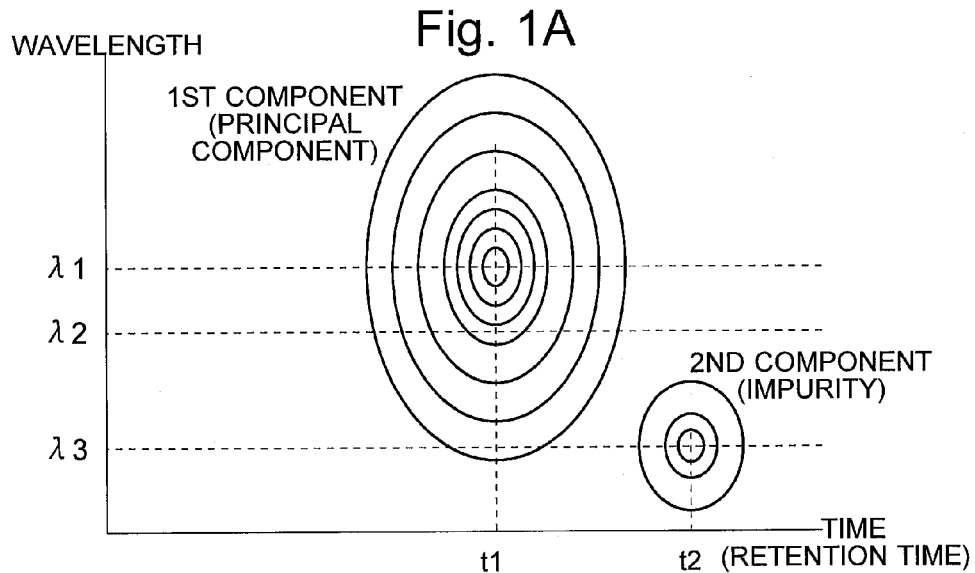
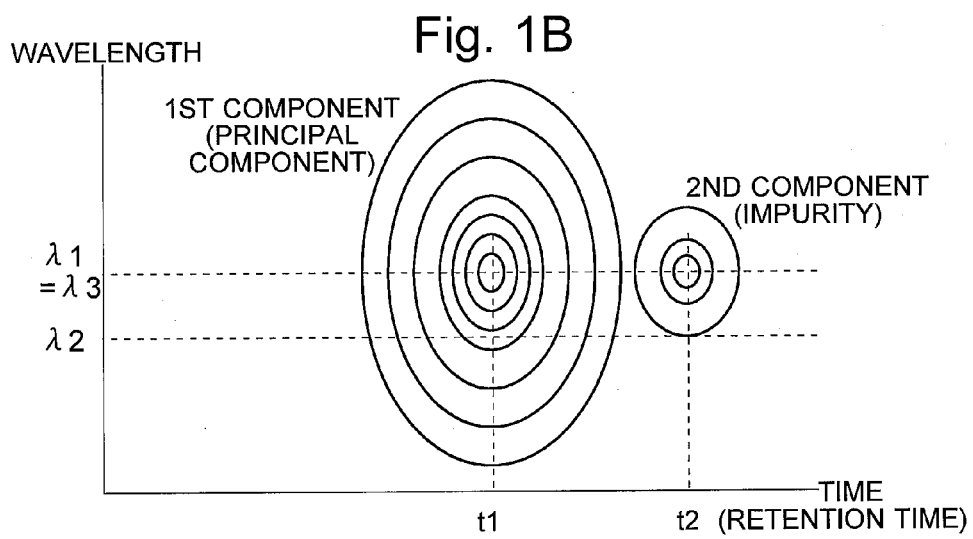
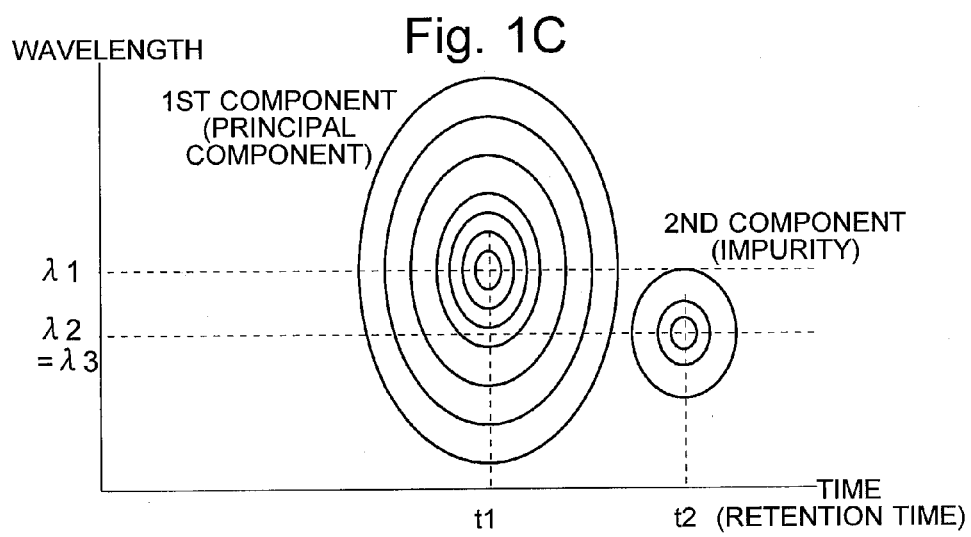

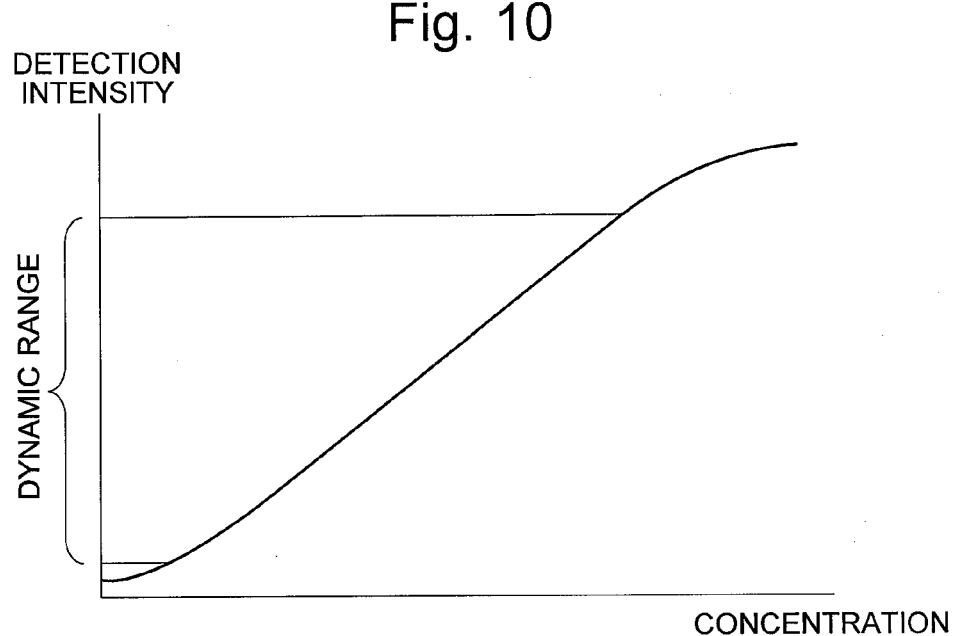

DATA PROCESSING SYSTEM AND DATA PROCESSING METHOD FOR CHROMATOGRAPH

CROSS REFERENCE TO RELATED APPLICATIONS

This application is a National Stage of International Application No. PCT/JP2013/079533 filed Oct. 31, 2013, claiming priority based on Japanese Patent Application No. 2012-267981 filed Dec. 7, 2012, the contents of all of which are incorporated herein by reference in their entirety.

TECHNICAL FIELD

The present invention relates to a data processing system and data processing method for a chromatograph apparatus, such as a liquid chromatograph or gas chromatograph.

BACKGROUND ART

In a chromatograph apparatus, a set of data which represents a chromatogram with the horizontal axis indicating the time and the vertical axis indicating the signal intensity (e.g. output voltage) can be obtained by an analysis of a sample (such data are hereinafter called the "chromatogram data"). In a data processing system for a chromatograph, a peak which appears on such a chromatogram is detected and a substance corresponding to the peak is identified from the peak position (retention time) with reference to a previously set identification table. Furthermore, the concentration and/or quantity of the substance is calculated from the height or area of the peak.

Such a data processing system normally has some restrictions of the level of the signal that can be processed, due to hardware limitations on the signal-processing circuits including an A/D converter. For an input of a signal whose level is above the upper limit or below the lower limit, the system cannot perform correct calculations.

Besides such a limitation concerning the signal processing, there is another problem that a detection result obtained with a detector for a chromatograph apparatus varies with the signal level. For example, in a device used as a detector for a liquid chromatograph (such as an ultraviolet-visible spectrophotometer or photodiode array detector), the non-linearity of the signal intensity normally becomes more noticeable as the component concentration in the sample increases (as shown in FIG. 10), which lowers the accuracy of quantitative determination. Meanwhile, the signal inevitably has various noises superposed on it. Accordingly, when performing an analysis, it is preferable to prepare the sample so that the concentrations of its components will be included in a predetermined range (dynamic range).

CITATION LIST

Non Patent Literature

Non Patent Literature 1: The Japanese Pharmacopoeia, Sixteenth Edition, [online], Mar. 24, 2011, The Ministry of Health, Labor and Welfare, [accessed on Sep. 25, 2012], the Internet

SUMMARY OF INVENTION

Technical Problem

One of the applications of liquid chromatographs is an impurity analysis for analyzing the proportion of an impurity relative to a principal component. For example, impurity analyses are frequently performed for drugs or similar products.

If the concentrations of the components to be analyzed in the sample are not significantly different, the analysis parameters (e.g. the concentration of the sample and the sensitivity of the detector) only need to be set so that all the target components will be included in the dynamic range. By contrast, if there is a considerable difference in the concentration among the target components, it is impossible to correctly perform the measurement; i.e. setting the parameters for correctly detecting the lowest-concentration component (impurity) causes distortion or saturation of the signal corresponding to the highest-concentration component (principal component), while setting the parameters for correctly detecting the highest-concentration component (impurity) causes the lowest-concentration component (impurity) to be obscured by noises.

For example, the Japanese Pharmacopeia, Sixteenth Edition (Non-Patent Literature 1) includes a section titled "Acetylcysteine: Purity (6) Related Substances" (pp. 311-312 in the Japanese version, or pp. 322-323 in the English version), which states that the substances other than acetylcysteine should satisfy the requirements that the peak area of each substance should not be higher than 0.3% and the total area of the peaks should not be higher than 0.6% on a chromatogram obtained by a test using a liquid chromatograph coupled with an ultraviolet absorptiometer with the measurement wavelength set at 220 nm. In one conventional method for correctly measuring the ratios of concentration of the components with such a large difference in concentration, a low-concentration sample and a high-concentration sample are prepared, and the measurement results obtained by performing an analysis multiple times are corrected according to the dilution ratios to determine the concentrations of the target components (or their ratios of concentration). In another conventional method, two cells with different optical path lengths are respectively set in two detectors, and an optical path length correction is performed to determine the concentrations of the target components (or their ratios of concentration) by a single analysis.

The problem to be solved by the present invention is to determine the concentration (or ratio of concentration) of a target component over a broad absorbance range by a single analysis and with a single detector.

Solution to Problem

A data processing system for a chromatograph according to the present invention aimed at solving the previously described problem includes:

a) a sensitivity coefficient holder for holding a value R of a sensitivity coefficient for a wavelength $\lambda 1$ belonging to one peak in a spectrum of a first component and a second wavelength $\lambda 2$ belonging to the same peak and having a lower intensity than $\lambda 1$, the value R defined using the ratio of the peak areas or similar information of two chromatograms respectively obtained at the two wavelengths;

b) a spectroscopic analyzer for spectroscopically analyzing a sample exiting from a component-separating column and for measuring an intensity at the second wavelength $\lambda 2$ of the spectrum of the first component and an intensity at a wavelength $\lambda 3$ of a spectrum of a second component at each point in time; and c) a concentration ratio calculator for calculating the ratio of concentration between the first component and the second component from: a chromatogram peak top height h1 and/or peak area A1 of the first component calculated from a peak height h2 and/or peak area A2 of a chromatogram peak corresponding to the spectrum peak of the first component at the second wavelength λ2 and the value R of the sensitivity coefficient; and a peak height h3 and/or peak area A3 of a chromatogram peak at the wavelength λ3.

A data processing method for a chromatograph according to the present invention aimed at solving the previously described problem includes the steps of:

a) holding a value R of a sensitivity coefficient for a wavelength λ1 belonging to one peak in a spectrum of a first component and a second wavelength λ2 belonging to the same peak and having a lower intensity than λ1, the value R defined using the ratio of the peak areas or similar information of two chromatograms respectively obtained at the two wavelengths;

b) spectroscopically analyzing a sample exiting from a component-separating column, and measuring an intensity at the second wavelength λ2 of the spectrum of the first component and an intensity at a wavelength λ3 of a spectrum of a second component at each point in time; and c) calculating the ratio of concentration between the first component and the second component from: a chromatogram peak top height h1 and/or peak area A1 of the first component calculated from a peak height h2 and/or peak area A2 of a chromatogram peak corresponding to the spectrum peak of the first component at the second wavelength λ2 and the value R of the sensitivity coefficient; and a peak height h3 and/or peak area A3 of a chromatogram peak at the wavelength λ3.

A spectrum of a certain component inherently has a specific shape to that component, and this shape is independent of the level of concentration of the component. Due to this similarity in the spectrum shape, in chromatograms too, the chromatogram peak areas at different wavelengths belonging to one spectrum peak have a fixed relationship. Accordingly, as described earlier, it is possible to previously determine and hold a value R of the sensitivity coefficient for a wavelength λ1 belonging to one peak on a spectrum of a first component and a second wavelength λ2 belonging to the same peak and having a lower intensity than λ1, the value R defined using the ratio of the peak area or other information of two chromatograms respectively obtained at the two wavelengths (which may be the ratio of any value indicative of the magnitude of a chromatogram peak, such as a peak-height ratio, other than the area ratio).

When the second wavelength λ2 having a lower intensity is thus used for the first component having a higher concentration, the intensity of the first component can be included in the dynamic range of the chromatograph apparatus simultaneously with the intensity at the wavelength λ3 of the second component having a lower concentration. Therefore, both components can be analyzed in a single analysis with a single chromatograph apparatus (see FIG. 1A). Subsequently, the concentration of the first component can be determined by making a correction between the wavelengths λ1 and λ2 by calculation using the sensitivity coefficient R. The concentration of the second component can be measured by a conventional method. Thus, the ratio of concentration between the first and second components can be obtained.

The measurement wavelength λ3 for the second component may coincide with the measurement wavelength λ1 for the first component (FIG. 1B). Alternatively, the measurement wavelength λ3 for the second component may coincide with the measurement wavelength λ2 (FIG. 1C).

In FIGS. 1A-1C, for ease of comprehension, λ1 is set at the peak top wavelength of the first component while λ3 is set at the peak top wavelength of the second component. However, λ1 and λ3 are not limited to the peak top wavelengths.

In the case where the concentrations of the components in a sample to be analyzed (particularly, the components which are likely to have high concentrations) are unknown, it is possible to simultaneously measure the intensities of all the wavelength components of the dispersed light using a photodiode array (PDA) detector or similar device in the chromatographic measurement and perform the previously described process based on the obtained three-dimensional data of time, wavelength and intensity. Specifically, if the intensity at the peak top wavelength λ1 of the peak of the first component has exceeded a predetermined upper limit intensity, a chromatogram at a wavelength λ2 which belongs to the same peak and which does not exceed the upper limit intensity is created and its peak height and/or peak area is measured. By correcting this peak height and/or peak area with the sensitivity coefficient R, the concentration of the first component can be determined. By comparing this concentration with that of the second component calculated from the peak height and/or peak area of the chromatogram at the peak top of the second component, the ratio of concentration between the first and second components can be obtained.

In general, impurities in drugs are generated during the production and storage processes of the drugs. Examples of impurities include the byproducts and intermediate products which are generated when drugs are produced, and the breakdown products which are generated while drugs are stored. Those impurities have similar structures to those of the drugs (and hence the name "Related Substances"). Therefore, the impurities have absorption characteristics similar to those of the principal component.

The previously described technique is a solution to the problem related to the case of performing a measurement for two components with a considerable difference in concentration. The essence of that solution exists in the idea of using the similarity in the spectrum shape to expand the dynamic range. Therefore, the present invention can be applied for any number of peaks whose peak heights exceed the dynamic range. Thus, a data processing system for a chromatograph according to the second aspect of the present invention includes the following elements operating on the basis of the three-dimensional data of time, wavelength and intensity obtained with a three-dimensional chromatograph:

a) a correction-needing peak detector for detecting a correction-needing peak which is a peak having a peak top intensity exceeding a predetermined threshold in a chromatogram at a target wavelength λ1;

b) a correction value calculator for calculating a corrected peak height and/or corrected peak area which is the peak height and/or peak area of the correction-needing peak in a chromatogram along a correction wavelength λ2 which is a wavelength different from the target wavelength λ1;

c) a sensitivity coefficient calculator for calculating, from a spectrum of the correction-needing peak obtained at time Ts which is earlier or later than the retention time T1 of the correction-needing peak and which belongs to the correction-needing peak, a value R of a sensitivity coefficient defined using the ratio between an intensity at the target wavelength λ1 and an intensity at the correction wavelength λ2 or similar information; and d) a peak value calculator for calculating the peak height and/or peak area of the correction-needing peak, based on the value R of the sensitivity coefficient and the corrected peak height and/or corrected peak area.

A data processing method for a chromatograph according to the second aspect of the present invention includes the following steps performed on the basis of the three-dimensional data of time, wavelength and intensity obtained with a three-dimensional chromatograph:

a) a correction-needing peak detection step, in which a correction-needing peak, which is a peak having a peak top intensity exceeding a predetermined threshold, is detected in a chromatogram at a target wavelength $\lambda 1$;

b) a correction value calculation step, in which a corrected peak height and/or corrected peak area is calculated, which is the peak height and/or peak area of the correction-needing peak in a chromatogram along a correction wavelength $\lambda 2$ which is a wavelength different from the target wavelength $\lambda 1$;

c) a sensitivity coefficient calculation step, in which a value R of a sensitivity coefficient defined using the ratio between an intensity at the target wavelength $\lambda 1$ and an intensity at the correction wavelength $\lambda 2$ or similar information is calculated from a spectrum of the correction-needing peak obtained at time Ts which is earlier or later than the retention time T1 of the correction-needing peak and which belongs to the correction-needing peak; and d) a peak value calculation step, in which the peak height and/or peak area of the correction-needing peak is calculated based on the value R of the sensitivity coefficient and the corrected peak height and/or corrected peak area.

The relationship between the target wavelength $\lambda 1$, correction wavelength $\lambda 2$ and other parameters for a correction-needing peak in the data processing system and method for a chromatogram according to this aspect of the present invention will be as shown in FIG. 2.

In this aspect of the present invention, the point in time at which a spectrum is obtained by a sensitivity coefficient calculator or in a sensitivity coefficient calculation step should preferably be later than the retention time of the correction-needing peak, since this choice provides a more stable elution of the components and a higher level of accuracy of the sensitivity coefficient.

Advantageous Effects of the Invention

With the data processing system for a chromatograph or data processing method for a chromatograph according to the present invention, it is possible to determine the concentration (or ratio of concentration) of each of the target components over a broad absorbance range by a single analysis and with a single detector. Therefore, the analysis can be completed within a short period of time. Furthermore, the cost of the system can be reduced due to its simple configuration.

BRIEF DESCRIPTION OF DRAWINGS

FIGS. 1A-1C are time-wavelength graphs conceptually showing the process performed by the data processing system and method for a chromatograph according to the first aspect of the present invention, where FIG. 1A is the case where the wavelengths $\lambda 1$ and $\lambda 2$ related to the first component are different from the wavelength $\lambda 3$ related to the second component, FIG. 1B is the case where $\lambda 1$ coincides with $\lambda 3$, and FIG. 1C is the case where $\lambda 2$ coincides with $\lambda 3$.

FIG. 10 illustrates a dynamic range of a detector.

DESCRIPTION OF EMBODIMENTS

Figure 2:
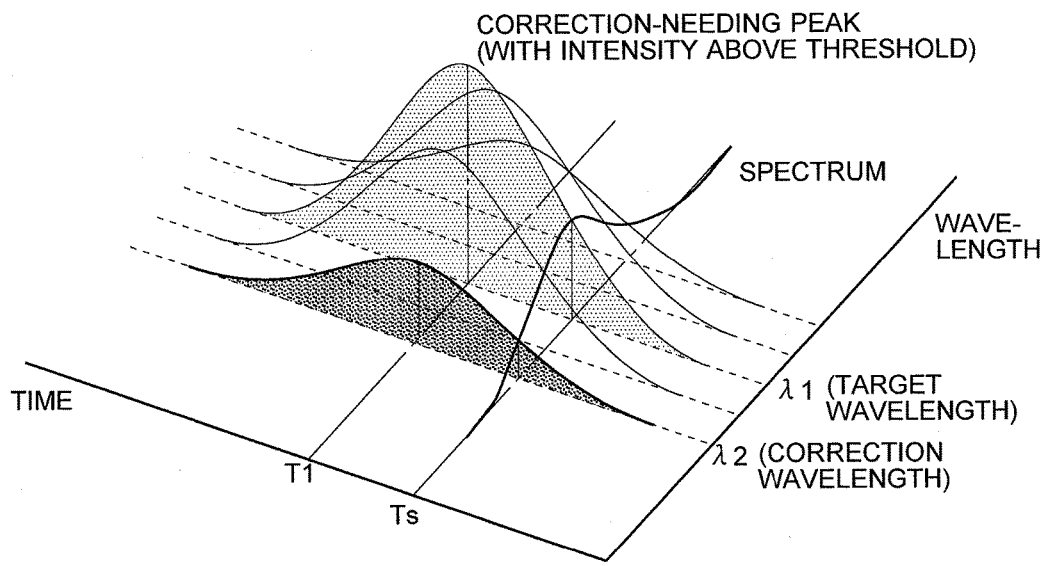
FIG. 2 is a three-dimensional graph of time, wavelength and intensity conceptually showing the process performed by the data processing system and method for a chromatograph according to the second aspect of the present invention.
Figure 3:
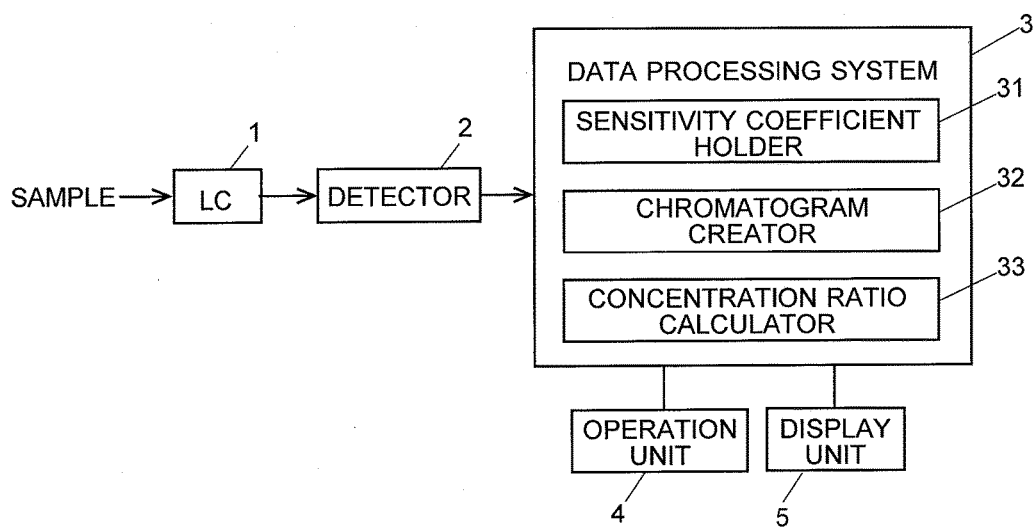
FIG. 3 is a schematic configuration diagram of an analyzing system including a data processing system for a chromatograph as the first embodiment.

One embodiment of the data processing system for a chromatograph according to the present invention is hereinafter specifically described with reference to the drawings. FIG. 3 is a schematic configuration diagram of an analyzing system including the data processing system for a chromatograph according to the present embodiment.

As shown in FIG. 3, this analyzing system has a liquid chromatograph (LC) 1 for temporally separating the components contained in a liquid sample, a detector 2 for detecting each of the separated components at predetermined wavelengths, and a data processing system 3 for processing the data produced by the detector 2. The data processing system 3 is actually a commonly used computer consisting of a CPU (central processing unit), memory unit, storage device (e.g. hard disc drives or solid state devices) and other components. A dedicated data processing software program is installed on this computer. By executing this software program, the functions of the chromatogram creator 32, concentration ratio calculator 33 and other components shown in the figure are realized. On the other hand, the sensitivity coefficient holder 31 is provided on one area of the storage device included in or connected to the data processing system 3.

Additionally, an operation unit 4 consisting of a keyboard and/or a pointing device (e.g. mouse) and a display unit 5 are connected to the data processing system 3.

In the sensitivity coefficient holder 31, a value R of the sensitivity coefficient for a sample which is known to contain a principal component is stored, with the peak top wavelength $\lambda 1$ of the principal component and a second wavelength $\lambda 2$ having a lower intensity than the peak top wavelength $\lambda 1$ as the target wavelengths. As the sensitivity coefficient R, the area ratio between the chromatograms at wavelengths $\lambda 1$ and $\lambda 2$ may be previously obtained by actually using a standard sample containing the sample to be analyzed, or an intensity ratio between $\lambda 1$ and $\lambda 2$ in the spectrum of the principal component may be used as R. In the present example, the peak top wavelength is selected as one of the two wavelengths, although any wavelength $\lambda 1'$ having a comparatively high intensity may be combined with the wavelength $\lambda 2$ having a comparatively low intensity to calculate the ratio. It is also possible to hold a plurality of ratios R1, R2 and so on for three or more wavelengths.

Figure 4:
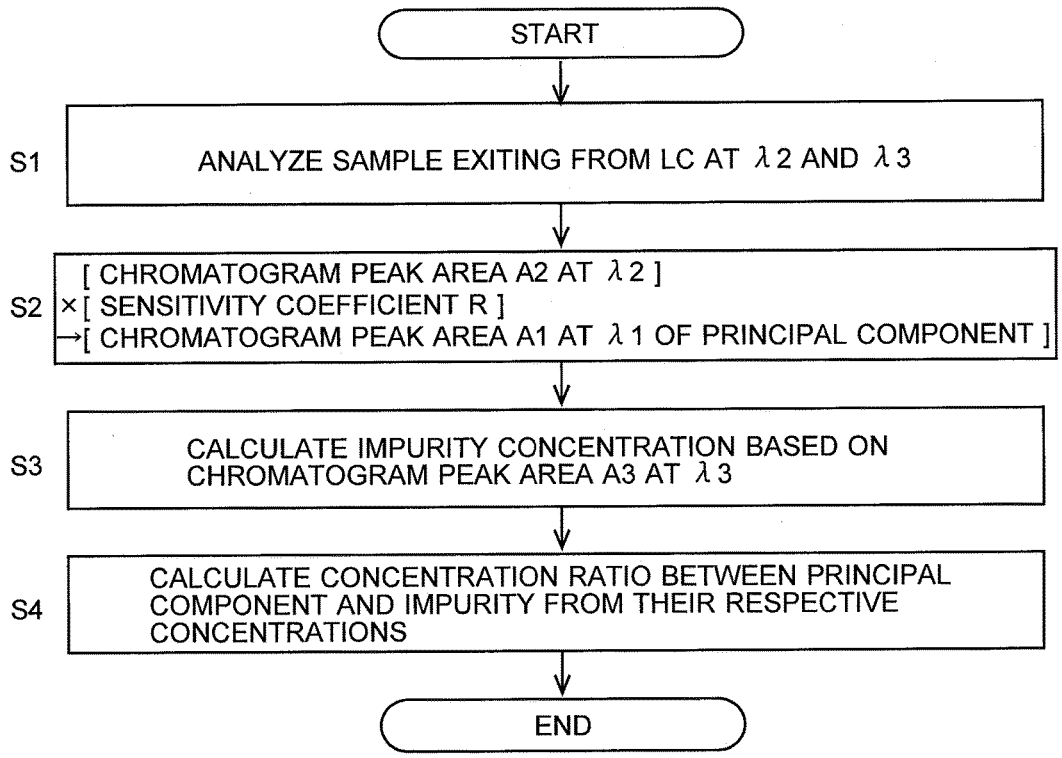
FIG. 4 is a schematic flowchart of the data processing performed in the data processing system for a chromatograph of the first embodiment.

A process of analyzing a sample which contains a principal component and its impurities and determining whether or not the content of the impurities relative to the principal component is equal to or greater than a predetermined upper limit level is hereinafter described with reference to the flowchart shown in FIG. 4.

Figure 5:
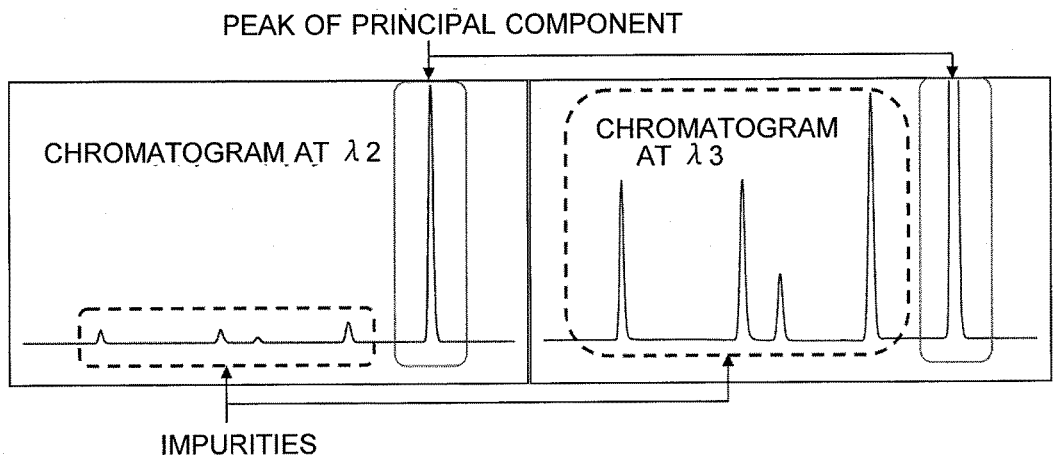
FIG. 5 shows two chromatograms obtained with the data processing system for a chromatograph of the first embodiment.
Figure 6:
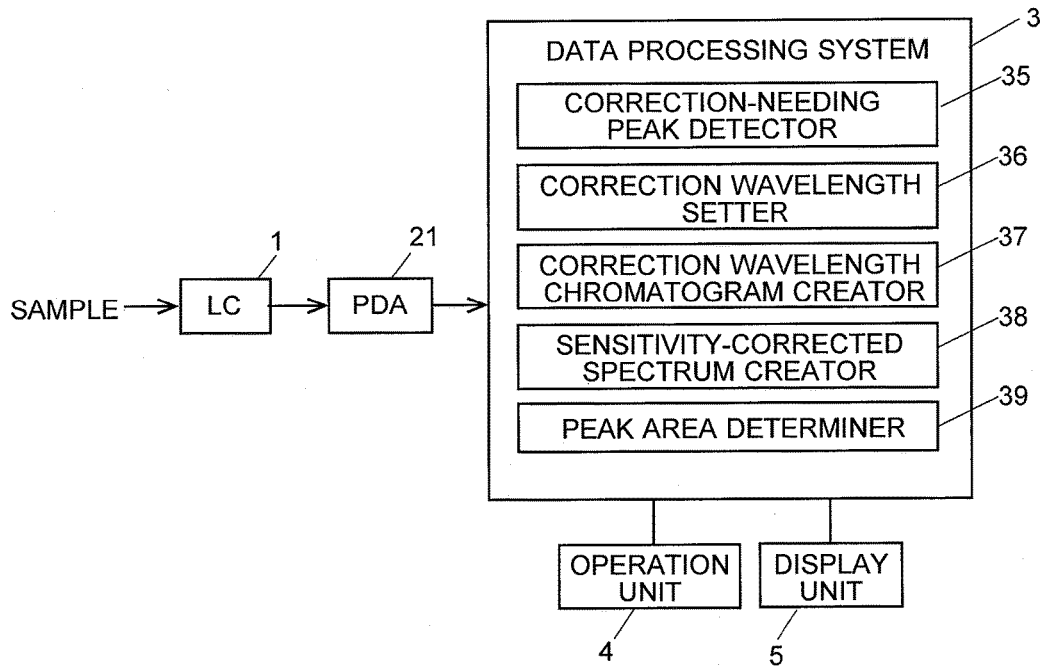
FIG. 6 is a schematic configuration diagram of an analyzing system including a data processing system for a chromatograph as an embodiment of the data processing system and method for a chromatograph according to the second aspect of the present invention.

Initially, the detection wavelengths of the detector 2 are set at the second and third wavelengths $\lambda 2$ and $\lambda 3$, and a sample to be analyzed is passed through the column of the LC1. The components of the sample are temporally separated by the LC1 and individually detected by the detector 2. At each point in time, the intensity values at the second and third wavelengths $\lambda 2$ and $\lambda 3$ are sent to the data processing system 3 (Step S1). Based on the signals successively fed from the detector 2, the chromatogram creator 32 in the data processing system 3 creates a chromatogram, as shown in FIG. 5. In FIG. 5, the left half is the chromatogram obtained at wavelength $\lambda 2$, while the right half is the chromatogram obtained at wavelength $\lambda 3$. In the chromatogram obtained at wavelength $\lambda 2$, the principal component forms a high peak, but its height (intensity) does not exceed the dynamic range (the vertical range in the figure). In the chromatogram obtained at wavelength $\lambda 3$, the peak height (intensity) of the principal component exceeds the dynamic range (the vertical range in the figure), while the impurity peaks show high values within the dynamic range, so that the concentrations of those impurities can be correctly measured using this chromatogram.

In the subsequent Step S2, the concentration ratio calculator 33 computes the chromatogram peak top area A1 of the principal component by multiplying the value R of the sensitivity coefficient stored in the sensitivity coefficient holder 31 and the area A2 of the chromatogram peak corresponding to the aforementioned spectrum peak of the principal component at the second wavelength $\lambda 2$ (i.e. the peak area of the principal component in the left chromatogram in FIG. 5).

In Step S3, the concentration ratio calculator 33 computes the concentration of the impurities based on the total area A3 of the chromatogram peaks at wavelength $\lambda 3$ (i.e. the Subsequently, in Step S4, the concentration ratio calculator 33 computes the ratio of concentration between the principal component and the impurities based on the concentration of the principal component calculated in Step S2 and that of the impurities calculated in Step S3 (Step S4).

As described thus far, the data processing system for a chromatograph according to the present invention can calculate the ratio of concentration between a principal component and impurities contained in a sample by a single analysis even if the difference in concentration between the principal component and the impurities is too large to determine the ratio between the two concentrations by a single measurement due to the limited dynamic range of the detector 2 or other reasons.

In the previous embodiment, it is previously known that the principal component is a high-concentration component and its peak top intensity at wavelength $\lambda 1$ will exceed the dynamic range of the detector 2. However, there is also the case where the components contained in the sample to be analyzed have unknown concentrations. Such a case can also be handled by simultaneously detecting the intensities of all the wavelength components of the dispersed light using a photodiode array (PDA) detector or the like in the chromatographic measurement and then performing the previously described process based on the obtained three-dimensional data of time, wavelength and intensity.

Specifically, if the peak intensity of the first component at the peak top wavelength $\lambda 1$ has exceeded a predetermined upper limit intensity, a chromatogram is created for wavelength $\lambda 2$ which belongs to the same peak and which does not exceed the upper limit intensity, and its area is measured. By correcting this area with the sensitivity coefficient R, the concentration of the first component can be determined. By comparing this concentration with that of the second component calculated from the area of the chromatogram at the peak top of the second component, the ratio of concentration between the first and second components can be obtained.

A data processing system for a chromatograph according to the second aspect of the present invention is hereinafter specifically described with reference to the drawings. The configuration of the entire system of the present embodiment is the same as that of the previous embodiment, except that a photodiode array (PDA) detector 21 is used as the detector. The data processing system of the present embodiment has a correction-needing peak detector 35, a correction wavelength setter 36, a correction wavelength chromatogram creator 37, a sensitivity-corrected spectrum creator 38, a peak area determiner 39 and other components. Using these components, the present system provides the function of virtually expanding the dynamic range in the detected chromatogram (dynamic range expanding function).

In an analysis of a high-concentration sample, a chromatogram peak may possibly exceed the highest measurable level for the detector or the upper limit of the linearity range of the detector and prevent the peak area value from being correctly obtained. In the PDA dynamic range expanding function of the data processing system for a chromatograph according to the present embodiment, the area value of a target peak is calculated by multiplying a peak area of a chromatogram taken at a wavelength where the linearity is ensured and a sensitivity coefficient R calculated from a spectrum taken at a point in the foot of the peak.

Specifically, the calculation is performed by the following procedure, in which all the peaks found in the chromatogram obtained at the target wavelength $\lambda 1$ are subjected to a correction process as follows:

(1) Detection of Correction-Needing Peak

For every peak belonging to the chromatogram obtained at the target wavelength $\lambda 1$, the correction-needing peak detector 35 obtains the peak intensity value and determines whether or not the intensity value exceeds a predetermined threshold. Any peak exceeding the threshold is identified as a correction-needing peak and is subjected to the correction process. The threshold should be previously set taking into account the dynamic ranges of the PDA, A/D converter and other components.

(2) Determination of Correction Wavelength

Figure 7:
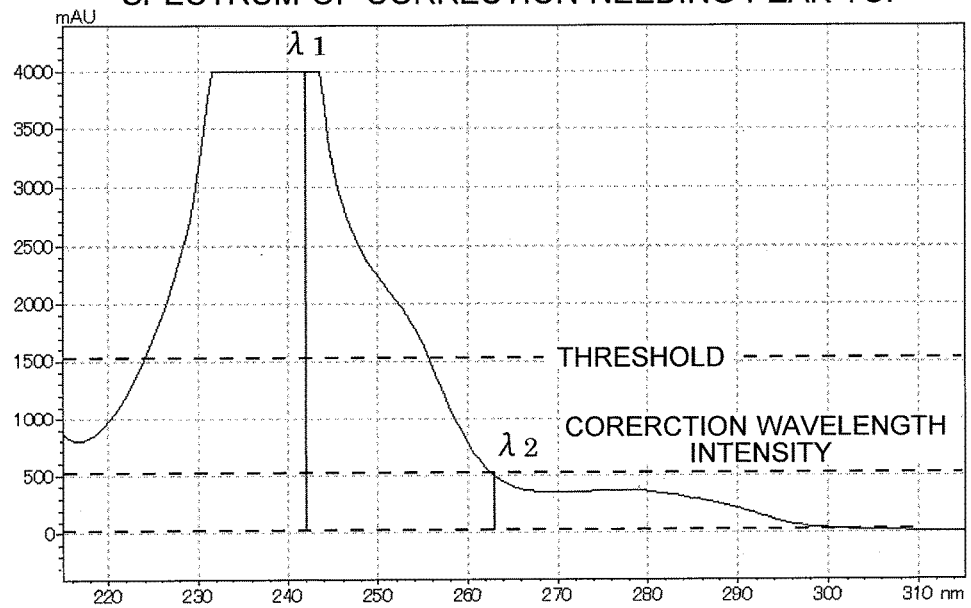
FIG. 7 shows a spectrum of a correction-needing peak to be processed in the embodiment of the second aspect.

The correction wavelength setter 36 sets a "correction wavelength" $\lambda 2$ which differs from the target wavelength $\lambda 1$ (FIG. 7). The correction wavelength $\lambda 2$ may be set automatically by the system or manually by the user.

following steps:

A spectrum is obtained at the retention time T1 of the correction-needing peak.

In this spectrum, a wavelength at which the intensity value becomes equal to a "correction wavelength intensity" (which is preset by the user) is located on either the plus side (longer-wavelength side) or minus side (shorter-wavelength side) of the absorption wavelength $\lambda 1$ and selected as the correction wavelength $\lambda 2$. The searching direction (plus or minus) may be previously specified by the user or defined beforehand in the system.

(3) Creation of Chromatogram at Correction Wavelength $\lambda 2$

The correction wavelength chromatogram creator 37 creates a chromatogram at the correction wavelength $\lambda 2$ from the three-dimensional data of the time, wavelength and intensity of the chromatogram obtained with the PDA 21, and searches this chromatogram for a peak corresponding to the correction-needing peak. The peak area A2 and peak height h2 of the located peak are adopted as the data for correction.

(4) Creation of Sensitivity-Corrected Spectrum

Figure 8:
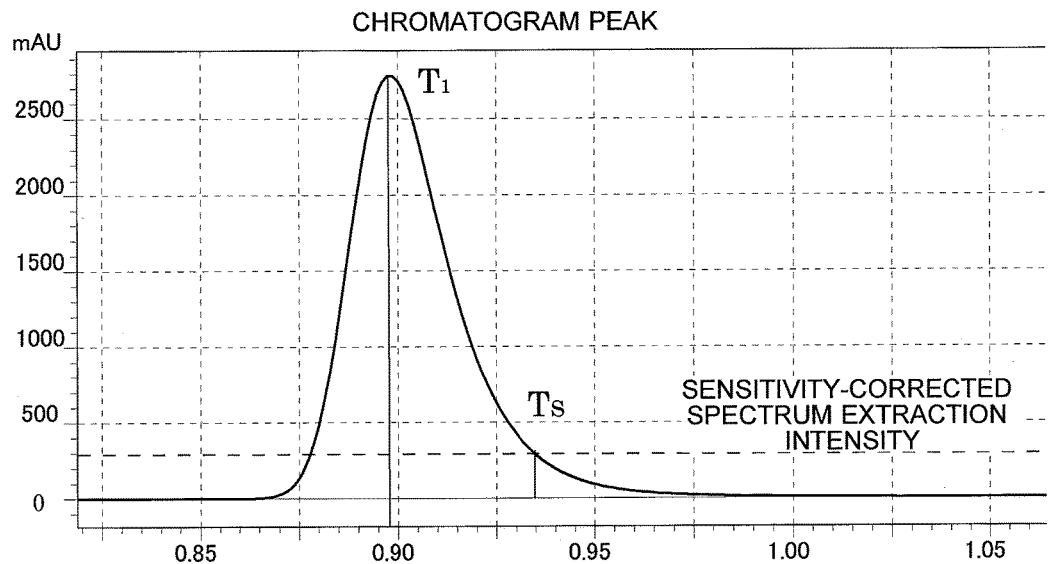
FIG. 8 shows a chromatogram including a correction-needing peak.
Figure 9:
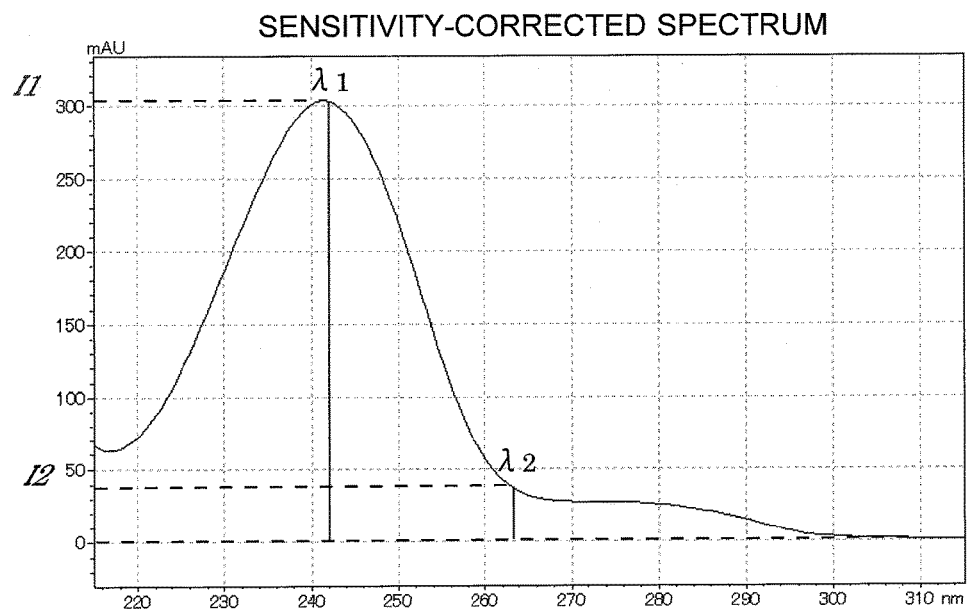
FIG. 9 shows a sensitivity-corrected spectrum.

From the aforementioned three-dimensional data, the sensitivity-corrected spectrum creator 38 creates a spectrum at a point in time Ts (FIG. 8) which is later than the retention time T1 of the correction-needing peak and at which the intensity value becomes equal to a predetermined "sensitivity-corrected spectrum extraction intensity" (this spectrum is called the "sensitivity-corrected spectrum"; FIG. 9). A background correction may additionally be performed on the created sensitivity-corrected spectrum.

(5) Calculation of Sensitivity Coefficient

The peak area determiner 39 initially calculates a "sensitivity coefficient R", which is the ratio between the intensity $I_1$ at wavelength $\lambda 1$ and the intensity $I_2$ at wavelength $\lambda 2$ in the sensitivity-corrected spectrum:

[Sensitivity Coefficient $R$]=[Intensity $I_1$ at Wavelength $\lambda 1$]/[Intensity $I_2$ at Wavelength $\lambda 2$]

(6) Determination of Area and Other Value of Correction-Needing Peak

Next, the peak area determiner 39 replaces the area A1 and height h1 of the correction-needing peak with the values obtained by multiplying the area A2 and height h2 of the peak of the chromatogram at the correction wavelength $\lambda 1$ by the sensitivity coefficient R:

[Area $A1$ of Correction-Needing Peak]=[Area $A2$ of Peak at Correction Wavelength $\lambda 2$]×[Sensitivity Coefficient $R$]

[Height $h1$ of Correction-Needing Peak]=[Height $h2$ of Peak at Correction Wavelength $\lambda 2$]×[Sensitivity Coefficient $R$]

Thus far, the data processing system for a chromatograph according to the present invention has been described, illustrating specific examples. It should be noted that the previous embodiments are mere examples and can be appropriately changed, improved or modified within the spirit of the present invention.

For example, it is possible to calculate not only the area of a saturated peak by a conversion from the area of a non-saturated peak as described in the previous embodiment, but also the area of a low peak by a conversion from the area of another peak located at a wavelength with a higher level of sensitivity. The type of chromatograph is not limited to the liquid chromatograph; it may naturally be a gas chromatograph.

REFERENCE SIGNS LIST

1 . . . Liquid Chromatograph (LC)
2 . . . Detector
21 . . . Photodiode Array (PDA) Detector
3 . . . Data Processing System
31 . . . Sensitivity Coefficient Holder
32 . . . Chromatogram Creator
33 . . . Concentration Ratio Calculator
35 . . . Correction-Needing Peak Detector
36 . . . Correction Wavelength Setter
37 . . . Correction Wavelength Chromatogram Creator
38 . . . Sensitivity-Corrected Spectrum Creator
39 . . . Peak Area Determiner
4 . . . Operation Unit
5 . . . Display Unit

The invention claimed is:

1. A data processing system for a chromatograph, comprising a memory unit, a single spectroscopic detector, and a central processing unit, wherein:
the memory unit holds a value R of a sensitivity coefficient for a first wavelength $\lambda 1$ belonging to one peak in a spectrum of a first component and a second wavelength $\lambda 2$ belonging to the same peak and having a lower intensity than $\lambda 1$, the value R defined using a ratio of peak areas or similar information of two chromatograms respectively obtained at the two wavelengths;
the single spectroscopic detector spectroscopically detects the first component and the second component contained in a sample provided for a single analysis exiting from a component-separating column and for measuring an intensity at the second wavelength $\lambda 2$ and an intensity at a third wavelength $\lambda 3$ at each point in time in the single analysis, when an intensity of the first component at the first wavelength $\lambda 1$ is outside of a dynamic range of the single spectroscopic detector; and
the central processing unit comprises:
a chromatogram creator for creating a chromatogram of the first component based on the intensity measured by the single spectroscopic detector at the second wavelength $\lambda 2$ and a chromatogram of the second component based on the intensity measured by the single spectroscopic detector at the third wavelength $\lambda 3$; and
a concentration ratio calculator for:
calculating a chromatogram peak height h1 of the first component at the first wavelength $\lambda 1$ from a chromatogram peak height h2 of a chromatogram peak of the first component at the second wavelength $\lambda 2$ and the value R of the sensitivity coefficient, calculating a concentration of the first component from the chromatogram peak height h1, and calculating a concentration of the second component from a peak height h3 of a chromatogram peak at the third wavelength $\lambda 3$ of the second component, or calculating a chromatogram peak area A1 of the first component at the first wavelength $\lambda 1$ from a chromatogram peak area A2 of a chromatogram peak of the first component at the second wavelength $\lambda 2$ and the value R of the sensitivity coefficient, calculating a concentration of the first component from the chromatogram peak area A1, and calculating a concentration of the second component from a peak area A3 of a chromatogram peak at the third wavelength $\lambda 3$ of the second component, and
calculating a ratio of concentration between the first component and the second component, and
wherein another spectroscopic detector is not used to detect the second component.

2. The data processing system for a chromatograph according to claim 1, wherein the third wavelength $\lambda 3$ coincides with the first wavelength $\lambda 1$.

3. The data processing system for a chromatograph according to claim 1, wherein the third wavelength $\lambda 3$ coincides with the second wavelength $\lambda 2$.

4. The data processing system for a chromatograph according to claim 1, wherein the memory unit further comprises an information of relationship between the concentration and the intensity and the peak height and/or the peak area of the peak in the chromatogram.

5. A data processing method for a chromatograph, comprising steps of:
   a) determining and holding a value R of a sensitivity coefficient for a first wavelength $\lambda 1$ belonging to one peak in a spectrum of a first component and a second wavelength $\lambda 2$ belonging to the same peak and having a lower intensity than $\lambda 1$, the value R defined using a ratio of a peak areas or similar information of two chromatograms respectively obtained at the two wavelengths;
   b) spectroscopically detecting, by a single spectroscopic detector, the first component and the second component contained in a sample provided for a single analysis exiting from a component-separating column, and measuring an intensity at the second wavelength $\lambda 2$ of the spectrum of the first component and an intensity at a third wavelength $\lambda 3$ at each point in time in the single analysis, when an intensity of the first component at the first wavelength $\lambda 1$ is outside of a dynamic range of the single spectroscopic detector;
   c) creating a chromatogram of the first component based on the intensity measured by the single spectroscopic detector at the second wavelength $\lambda 2$ and a chromatogram of the second component based on the intensity measured by the single spectroscopic detector at the third wavelength $\lambda 3$; and
   d) calculating a chromatogram peak height h1 of the first component at the first wavelength $\lambda 1$ from a chromatogram peak height h2 of a chromatogram peak of the first component at the second wavelength $\lambda 2$ and the value R of the sensitivity coefficient, calculating a concentration of the first component from the chromatogram peak height h1, and calculating a concentration of the second component from a peak height h3 of a chromatogram peak at the third wavelength k3 of the second component, or calculating a chromatogram peak area A1 of the first component at the first wavelength $\lambda 1$ from a chromatogram peak area A2 of a chromatogram peak of the first component at the second wavelength $\lambda 2$ and the value R of the sensitivity coefficient, calculating a concentration of the first component from the chromatogram peak area A1, and calculating a concentration of the second component form a peak area A3 of a chromatogram peak at the third wavelength $\lambda 3$ of the second component, and
   calculating a ratio of concentration between the first component and the second component,
   wherein another spectroscopic detector is not used to detect the second component.

6. The data processing method for a chromatograph according to claim 5, wherein the third wavelength $\lambda 3$ coincides with the first wavelength $\lambda 1$.

7. The data processing method for a chromatograph according to claim 5, wherein the third wavelength $\lambda 3$ coincides with the second wavelength $\lambda 2$.

8. The data processing method for a chromatograph according to claim 5, further comprising a step of holding an information of relationship between the concentration and the intensity and the peak height and/or the peak area of the peak in the chromatogram.

9. A data processing system for a chromatograph, comprising a single spectroscopic detector and a central processing unit operating on a basis of three-dimensional data of time, wavelength and intensity obtained with a three-dimensional chromatograph:
   the single spectroscopic detector for detecting a sample component exiting from a component-separating column, and measuring an intensity at a target wavelength $\lambda 1$ and an intensity at a correction wavelength $\lambda 2$ of the sample component by a single analysis, the correction wavelength $\lambda 2$ being different from the target wavelength $\lambda 1$;
   the central processing unit comprising:
      a chromatogram creator for creating a chromatogram based on the intensity measured by the single spectroscopic detector at the target wavelength $\lambda 1$ and a chromatogram based on the intensity measured by the single spectroscopic detector at the correction wavelength $\lambda 2$;
      a correction-needing peak detector for detecting a correction-needing peak which is a peak having a peak intensity being outside of a dynamic range of the single spectroscopic detector in the chromatogram at the target wavelength $\lambda 1$;
      a correction value calculator for calculating a corrected peak height and/or corrected peak area which is a peak height and/or peak area of the correction-needing peak in a chromatogram along the correction wavelength $\lambda 2$;
      a sensitivity coefficient calculator for calculating, from a spectrum of the correction-needing peak obtained at time Ts which is earlier or later than a retention time T1 of the correction-needing peak and which belongs to the correction-needing peak, a value R of a sensitivity coefficient defined using a ratio between an intensity at the target wavelength $\lambda 1$ and an intensity at the correction wavelength $\lambda 2$ or similar information; and
      a peak value calculator for calculating the peak height and/or peak area of the correction-needing peak, based on the value R of the sensitivity coefficient and the corrected peak height and/or corrected peak area.

10. A data processing method for a chromatograph, comprising following steps performed on a basis of three-dimensional data of time, wavelength and intensity obtained with a three-dimensional chromatograph:
    a) a single spectroscopic detecting step, in which a sample component exiting from a component-separating column is detected, and an intensity at a target wavelength $\lambda 1$ and an intensity at a correction wavelength $\lambda 2$ of the sample component are measured, the correction wavelength $\lambda 2$ being different from the target wavelength $\lambda 1$;
    b) a chromatogram creating step, in which a chromatogram is created based on the intensity measured at the target wavelength $\lambda 1$ and a chromatogram is created based on the intensity measured at the correction wavelength $\lambda 2$, respectively;
    c) a correction-needing peak detection step, in which a correction-needing peak, which is a peak having a peak intensity being outside of a dynamic range of the single spectroscopic detector, is detected in the chromatogram at the target wavelength $\lambda 1$;

d) a correction value calculation step, in which a corrected peak height and/or corrected peak area is calculated, which is a peak height and/or peak area of the correction-needing peak in the chromatogram along the correction wavelength $\lambda 2$ which is a wavelength different from the target wavelength $\lambda 1$;

e) a sensitivity coefficient calculation step, in which a value R of a sensitivity coefficient defined using a ratio between an intensity at the target wavelength $\lambda 1$ and an intensity at the correction wavelength $\lambda 2$ or similar information is calculated from a spectrum of the correction-needing peak obtained at time Ts which is earlier or later than a retention time T1 of the correction-needing peak and which belongs to the correction-needing peak; and f) a peak value calculation step, in which the peak height and/or peak area of the correction-needing peak is calculated based on the value R of the sensitivity coefficient and the corrected peak height and/or corrected peak area.

* * * * *